United States Patent [19]

Weil

[11] 4,400,537

[45] Aug. 23, 1983

[54] PROCESS FOR 1,4-PHENYLENEDIAMINE

[75] Inventor: Thomas A. Weil, Naperville, Ill.

[73] Assignee: Standard Oil Company (Indiana), Chicago, Ill.

[21] Appl. No.: 369,499

[22] Filed: Apr. 19, 1982

Related U.S. Application Data

[63] Continuation-in-part of Ser. No. 247,362, Mar. 25, 1981, abandoned, which is a continuation of Ser. No. 837,537, Sep. 28, 1977, abandoned.

[51] Int. Cl.$^3$ .............................................. C07C 85/06
[52] U.S. Cl. ................................... 564/402; 564/403; 564/437
[58] Field of Search ................................ 564/403, 402

[56] References Cited

U.S. PATENT DOCUMENTS 3,860,650  1/1975  Becker et al. .................. 564/403 X Primary Examiner—John Doll
Attorney, Agent, or Firm—William C. Clarke; William T. McClain; William H. Magidson

[57] ABSTRACT

A process for the preparation of 1,4-phenylenediamine from 1,4-dihydroxybenzene at a temperature within the range of from about 300° C. to 450° C. and a pressure of from atmospheric to 3000 psig in the presence of an aminating agent, an inert hydrocarbon and an acidic alumina catalyst. p-Aminophenol can be aminated to 1,4-phenylenediamine with the same process.

8 Claims, No Drawings

PROCESS FOR 1,4-PHENYLENEDIAMINE

This is a continuation-in-part of application Ser. No. 247,362, filed Mar. 25, 1981, which, in turn, is a continuation of Ser. No. 837,537, filed Sept. 28, 1977, both now abandoned.

BACKGROUND OF THE INVENTION

This process relates to an improved process for the preparation of 1,4-phenylenediamine using 1,4-dihydroxybenzene. p-Aminophenol can be aminated to 1,4-phenylenediamine with the same process. The process is accomplished in good yield at a temperature within the range of from about 300° C. to 450° C. at a pressure up to 3000 psig despite the fact that p-aminophenol, the intermediate compound in the amination of 1,4-dihydroxybenzene to 1,4-phenylenediamine sublimes and decomposes at temperatures within the range of from about 184° C. to about 284° C. and 760 mm pressure. The invented process is accordingly surprising although the direct amination of mono- and dihydroxybenzenes other than 1,4-dihydroxybenzene can be accomplished at temperatures within the range between 300° C. and 570° C., by the process taught by Becker, et al., U.S. Pat. No. 3,860,650. The preparation of 1,4-phenylenediamine from 1,4-dihydroxybenzene by the process taught by Becker U.S. Pat. No. 3,860,650 results in low uneconomical yields. The intermediate of p-aminophenol in conversion of 1,4-dihydroxybenzene to 1,4-phenylenediamine decomposes at the temperatures of 300° C. to 570° C. taught for the Becker U.S. Pat. No. 3,860,650 process.

Aromatic diamines are useful in the preparation of aromatic polyamides, polyimides and polyamideimides. Aromatic diamines are also well-known as being useful in the preparation of azo dye intermediates, photographic developing agents, fur dyes, agents for photochemical measurements, antioxidants for petroleum products, cellulose ethers and rubber.

Preparation of phenylenediamines has been by a number of processes which have been of two types; amination by reduction wherein a bond between a nitrogen and a ring carbon already exists in the molecule and amination by ammonolysis wherein a nitrogen is not already bonded to a ring carbon. The p-phenylenediamine is usually obtained by reduction of the parent nitro compound, p-nitroaniline, because of better yields, the need for avoiding contaminants, the sensitivity of the starting materials and final products to the conditions of the process. Reduction of the parent nitro compound requires preparation of the parent compound which involves a nitration step, usually of a chlorobenzene, which results in an ortho-para mixture. Amination by reduction and ammonolysis is performed with separation and purification of the isomers with consequent overall lowered yields. Consequently, for some time a more direct method of producing p-phenylenediamine has been sought.

I have found a method whereby 1,4-dihydroxybenzene can be converted to p-phenylenediamine in good yield without decomposition of the intermediate of p-aminophenol occurring and consequent loss of final product. The application of the process is directed only to the preparation of p-phenylenediamine from 1,4-dihydroxybenzene since aminophenols other than p-aminophenol do not decompose at the temperatures and pressures required for amination of 1,4-dihydroxybenzene.

It is already known that aniline-type compounds can be prepared by the liquid or vapor phase amination of certain phenolic compounds with ammonia. Generally, the reaction takes place at elevated pressures and temperatures between 300° C. and 600° C. in the presence of catalysts containing silica and alumina. These phenolic compounds or hydroxybenzenes can be unsubstituted or substituted so long as the substitutions do not interfere with the course of the reaction. Typical groups which can be attached to the benzene nucleus are alkyl or aryl groups. The type of catalyst employed and reaction conditions have been found to be of particular significance. For example, U.S. Pat. No. 3,860,650 to Becker et al. teaches the preparation of organic amines from certain phenolic-type compounds including hydroxybenzenes such as catechol, pyrolgallol and hydroquinone in the vapor or liquid phase at temperatures of from 300° C. to 570° C. in the presence of an alumina catalyst derived from a precipitated gel form and having a minimum alkali metal content which is achieved by leaching with acid. As an example, Becker recites the amination of a substituted phenolic-type compound, the preparation of 2,2-bis (p-aminophenyl) propane by the liquid phase amination of 4,4-isopropylidene bisphenol. Becker does not teach in an example the preparation of p-phenylenediamine using temperatures of from 300° C. to 570° C. U.S. Pat. No. 3,929,889 discloses the preparation in low yields of phenylenediamines predominantly meta or ortho and some quantities of para from aromatic monoamines such as aniline in the presence of a hydrogen transfer catalyst of a nickel/nickel oxide cataloreactant. In general, U.S. Pat. No. 3,929,889 teaches that cataloreactants and reaction conditions leading to higher conversion favor the predominant production of meta-phenylenediamines; those leading to lower conversion of aromatic monoamines favor the ortho-phenylenediamines. U.S. Pat. No. 3,931,298 also discloses a hydrogen transfer catalyst for the conversion of hydroxy aromatics to the corresponding aromatic amines with ammonia in the presence of a Group VIII metal hydrogen transfer catalyst with a cyclohexanone cocatalyst at a temperature of from about 200°–400° C. Liquid hydrocarbons can be used as solvents. Hydroquinone is recited as a starting material although preferred materials are mononuclear alkyl-substituted phenols. Japanese Pat. Nos. 74-14737 and 74-14738 teach methods of gas-phase preparation of aromatic amines and preparation of the gamma alumina catalysts used. p-Phenylenediamine is produced from hydroquinone in low yield as an example. The gamma alumina catalyst is required to be treated with a carboxylic acid to provide activity. Weakly acidic catalysts such as commercial gamma alumina without an acid treatment are stated to be too inactive to be of use. Alpha and eta aluminas are not to be used.

Accordingly, it is well-known in the prior art to aminate hydroxybenzenes usually to the monoamines, but an economical process for ammonolysis in high yields and good purity of 1,4-dihydroxybenzene to p-phenylenediamine has not been previously known. For example, a satisfactory process has yet to be developed for the ammonolysis of p-dichlorobenzene to the diamine by direct replacement of both chlorine atoms even though excellent yields can be obtained of the ortho compound from o-dichlorobenzene if the reactant is highly purified to remove the para compound. (Kirk- Othmer, *Ency. of Chem. Tech.*, 2nd Edition, Interscience, Vol. 2, 1963, p. 361.)

SUMMARY OF THE INVENTION

A process for the preparation in excellent yield of 1,4-phenylenediamine from 1,4-dihydroxybenzene by amination at a temperature within the range of from about 300° C. to 450° C. and a pressure of up to 3000 psig in the presence of ammonia, an inert hydrocarbon and an acidic alumina catalyst. p-Aminophenol can be aminated to 1,4-phenylenediamine by the same process.

DETAILED DESCRIPTION OF THE INVENTION

A process for the preparation of 1,4-phenylenediamine in excellent yield from 1,4-dihydroxybenzene by amination at a temperature within the range of from 300° C. to 450° C. and a pressure of up to 3000 psig in the presence of ammonia, an inert hydrocarbon and an acidic alumina catalyst.

The process of the invention is applicable only to the preparation of 1,4-phenylenediamine through the intermediate of p-aminophenol since p-aminophenol otherwise tends to decompose in the amination of 1,4-dihydroxybenzene to p-phenylenediamine at usual process temperatures.

Aminating agents other than ammonia which are applicable to the instant invention are hydrocarbon substituted amines. Anhydrous ammonia is preferred as the aminating agent although other compounds which yield ammonia can be used such as ammonium chloride, ammonium bromide, ammonium iodine, ammonium hydroxide, ammonium nitrate, ammonium carbonate and the like. Also useful as aminating agents are the hydrocarbon substituted primary and secondary amines such as methylamine, dimethylamine, ethylamine and diethylamine.

On a mole basis, a large excess of aminating agent such as ammonia is required. A mole ratio of greater than 20:1 of aminating agent, as ammonia, to reactant is required. As ammonia, the ratio of aminating agent to reactant is preferably at least 25:1. A more preferred ratio is from about 70:1 to about 150:1 moles of ammonia to moles of reactant. Below the ratio of 70:1, the yield of diamine product is low. The upper range is limited by the economics of recovering the excess ammonia after passing through the reactor, by the reactor size and by reaction pressure.

The use of an inert hydrocarbon is essential. The inert hydrocarbon is necessarily inert or relatively inert to the course of the reaction. Without use of an inert hydrocarbon, a good yield of p-phenylenediamine is not obtained. Since p-aminophenol decomposes at 184°–186° C. to form polymeric compounds, it is surprising that the presence of the inert hydrocarbon prevents decomposition of p-aminophenol, the intermediate in the preparation of p-phenylenediamine from 1,4-dihydroxybenzene, thus increasing the yield of p-phenylenediamine to an economical, high level.

Generally, any inert, nonreactive hydrocarbon compound or ether compound can be used which has a boiling point within the range of 25° C. to 400° C., solubilizes 1,4-dihydroxybenzene and p-aminophenol, and will not undergo amination or decomposition under the conditions of the reaction. Compounds which are otherwise suitable but which react under the conditions of the reaction can be used if the reaction products are desired. For example, halogenated hydrocarbons such as the chlorobenzenes, bromobenzenes and iodobenzenes can be used even though amine derivatives of these compounds result. Fluorocarbons would be less likely to react. Phenols and aliphatic alcohols react to give the corresponding amine if used, i.e., phenol yields aniline and methanol yields methylamine. Carbonyl and nitrile compounds give a mixture of reaction products because of reaction with ammonia under the reaction conditions. Organic acids may be suitable even though acid derivatives are present in the reaction product mixture. Amines such as aniline, aliphatic primary, secondary and tertiary amines as well as pyridines and other heterocyclic nitrogen compounds as well as others may be used.

Preferred liquid hydrocarbon compounds are those with a boiling point in the approximate range of from 50°–200° C. and which are relatively inert to the reactants because they do not have reactive hydrogens or other reactive substituents. Compounds with a boiling point below 25° C. cause development of excessive pressures within the reactor and require uneconomic reactor construction to withstand the resulting pressures. Compounds with boiling points over 400° C. develop low reactor pressures but can be difficult to separate from the reaction mix and resulting products. Preferred hydrocarbons are hexane, heptane, octane, nonane, decane, benzene, toluene, xylene, and cyclohexane. Other compounds which can be used are diglyme, dioxane, ethylbenzene, cumene, trimethylbenzenes, furan, tetrahydrofuran, phenyl ether, petroleum ethers and Dowtherm.

The use of an acidic dehydrating catalyst is required but a highly acidic catalyst is not desired. A high catalyst concentration is required, i.e., a substantial amount of catalyst relative to the amount of reactants. Commercially available alumina catalysts of alpha, gamma or eta alumina are suitable although the gamma alumina is preferred. A silica-alumina catalyst in which the alumina is deposited upon a silica base can be used. Catalysts commercially available and useful in the process are Areo 100 gamma alumina and Areo 1000 gamma alumina made by the American Cyanamid Corporation; T-1732 and T-374 gamma alumina prepared by the Girdler Corporation; Catapal SB prepared by Conoco; and Kaiser KSA alumina made by the Kaiser Corporation. The preferred catalyst is stated to have a surface area of at least 150 square meters per gram and can be activated by heating to 1000° F. for a period of 1 to 3 hours. Catalyst size conveniently can be in $\frac{1}{8}$-inch extruded pellets or 20 to 40 mesh (U.S.) particles, but any physical form from powder to pellet can be used.

Catalyst concentration relative to reactants can be of the range of 1:1 to 1:10, weight of reactant to weight of catalyst. Preferred weight range of reactant to catalyst is 1:1 to 1:5, reactant to catalyst.

The reaction proceeds at an elevated temperature, the limits of which are from about 300° C. to 450° C. The preferred operating temperature is within the range of from about 300° C. to about 385° C. Below 300° C. the reaction is very slow. Above 385° C. the yield of the diamine product diminishes.

The reaction can be carried out as a batch or continuous process. In a batch operation, 1,4-dihydroxybenzene, catalyst, an inert hydrocarbon and ammonia are mixed together and heated in a sealed pressure vessel to reaction temperature. Amination is usually completed in 1 to 4 hours. Optionally, 1,4-dihydroxybenzene, the inert hydrocarbon and catalyst can be mixed together in a closed vessel which is heated to reaction temperature while being mixed and the ammonia added over an extended period of time.

In the continuous method, 1,4-dihydroxybenzene, the inert hydrocarbon and ammonia are passed through a fixed bed of catalyst maintained at reaction temperature at a space velocity such that residence time is sufficient to provide conversion to the aromatic diamine.

Pressures are not critical so long as they suffice to cause amination. Pressures up to 3000 psig are used.

After the reaction is completed, the product is recovered by removing the catalyst by filtration and distilling off the inert hydrocarbon. The catalyst is washed with organic solvents to remove any organic impurities and then can be reused. If necessary, the catalyst can be reactivated by heating.

In summary, the invention comprises a process for the amination of 1,4-dihydroxybenzene to 1,4-phenylenediamine in high yield in the presence of an aminating agent, preferably ammonia, an inert hydrocarbon and an acidic alumina catalyst, at a temperature within the range of 300° C. to 450° C., a pressure of up to 3000 psig. p-Aminophenol can also be used as a starting material because it is the intermediate in preparation of 1,4-phenylenediamine from 1,4-dihydroxybenzene.

Required mole ratio of aminating agent as ammonia to reactant, 1,4-dihydroxybenzene or p-aminophenol, as starting material, is at least 20:1, aminating agent to reactant. Preferred mole ratio range is from about 70:1 to about 150:1. Weight ratio of reactant to catalyst can be of the range of 1:1 to 1:10; preferred weight ratio is from about 1:1 to about 1:5, reactant to catalyst. Preferred inert hydrocarbons are liquids which do not have reactive hydrogens. Preferred hydrocarbons are benzene, toluene or xylene.

The following examples are given by way of illustration and are not intended to limit the scope of the invention.

EXAMPLE I

The following example illustrates the process of the invention wherein a total yield of 86.1% of aminated product was obtained.

To a 1 gal. stirred stainless steel autoclave were charged 20 g of Areo 100 gamma alumina and 1.2 liters benzene. The autoclave was sealed, flushed with nitrogen, followed by ammonia. 61.2 g (3.6 moles) of ammonia were then charged into the autoclave and the system heated to 350° C. with stirring by impeller. After the reactor was heated to reaction conditions (350° C. and 1500 psi), 4 g ($3.6 \times 10^{-2}$ mole) of 1,4-dihydroxybenzene were charged. Ratio of ammonia to 1,4-dihydroxybenzene was 100:1. The stirring was continued for one hour with temperature at 350° C. and pressure at 1400 psi. At the end of this period, the reactor was rapidly cooled to room temperature, the excess ammonia vented and reactor contents removed. The catalyst was removed from the reaction mixture by filtration and the volume of the reaction mixture decreased causing crystallization of the product. Crystalline product recovered from the reaction solution was shown to be 97% p-phenylenediamine and 2% p-aminophenol by silylation gas chromatographic analysis. Complete evaporation of the reaction mixture gave another 0.5 g of solids which was 59% p-phenylenediamine. A further 0.5 g of product was recovered by washing the reactor and catalyst with methanol. This material was 80% p-phenylenediamine. The overall yield of p-phenylenediamine was 84.3% plus a yield of 1.8% p-aminophenol at complete 1,4-dihydroxybenzene conversion for a total yield of 86.1%.

EXAMPLE II

Four grams ($3.6 \times 10^{-3}$ moles) of 1,4-dihydroxybenzene and 38.4 g (2.3 moles) ammonia were reacted in 1.2 liters benzene with 20 g Areo 100 alumina as described in Example I. Ratio of ammonia to 1,4-dihydroxybenzene was 64:1. A reaction temperature of 335° C. and a pressure of 1525 psig were held for one hour. Upon cooling and workup as described in Example I, 3.92 g of product were recovered. Analysis of product by silylation gas chromatographic analysis indicated a 65% yield of p-phenylenediamine and 30% yield of p-aminophenol, for a total yield of 95%.

The above data show the effects of a lower mole ratio of ammonia to 1,4-dihydroxybenzene and temperature upon p-aminophenol and p-phenylenediamine yields, e.g., that at a mole ratio of 65:1 of ammonia to 1,4-dihydroxybenzene a temperature of 335° C., and the amination of 1,4-dihydroxybenzene to p-phenylenediamine through the intermediate p-aminophenol is less complete. The yield of p-phenylenediamine is decreased and the yield of p-aminophenol is increased. Total yield of 95% indicates little decomposition of p-aminophenol occurred.

EXAMPLE III

The following Example III and Examples IV and V illustrate that p-aminophenol, under the conditions of the instant invented process, can be aminated in good yield to p-phenylenediamine although p-aminophenol can decompose at temperatures greater than 284° C.

To a 1 gal. stirred stainless steel autoclave were charged 20 g of Areo 100 gamma alumina and 1.2 liters benzene. The autoclave was sealed, flushed with nitrogen, followed by ammonia. 61.2 g (3.6 moles) of ammonia were then charged into the autoclave and the system heated to 350° C. with stirring. After the reactor was heated to reaction conditions (350° C. and 1500 psig), 4 g ($3.7 \times 10^{-2}$ moles) of solid p-aminophenol were charged. The stirring was continued for one hour with the temperature at 350° C. At the end of this period the reactor was rapidly cooled to room temperature, the excess ammonia vented and the reactor contents removed. The catalyst was removed from the reaction mixture by filtration and the volume of the reaction solution decreased causing crystallization of 2.5 g of product. The product was approximately 92% p-phenylenediamine and 7% p-aminophenol. Five other minor impurities amounted to approximately 1.0%, as shown by silylation gas chromatography. Complete evaporation of the remaining filtrate gave a small amount of impure product. The reactor and catalyst were washed with methanol, giving an additional 0.9 g of solid product which was 50% p-phenylenediamine and 40% p-aminophenol. The overall yield of p-phenylenediamine based on original weight of the reactant (4 g) sample was 72% at 86% p-aminophenol conversion and 83% selectivity.

EXAMPLE IV

To a 300 ml stainless steel rocking autoclave were charged 1 g ($9.2 \times 10^{-3}$ moles) of p-aminophenol, 20 ml of benzene and 5 g Areo 100 gamma alumina. After the autoclave was sealed and flushed with nitrogen, followed by ammonia, 14 g (0.6 mole) of ammonia were charged into the autoclave. The autoclave was then heated to 350° C. for one hour during which time an internal pressure of 1400 psig was generated. After one hour at 350° C. the autoclave was allowed to cool for several hours, the excess pressure vented and the contents removed. The catalyst was recovered by filtration and washed with benzene and methanol to remove any organic material. The solvent was removed by distillation leaving a solid product. Silylation gas chromatographic analysis of the product indicated p-phenylenediamine yield was 73% at 76% selectivity.

EXAMPLE V

In the procedure of Example IV but with a different catalyst, one g ($9.2 \times 10^{-3}$ moles) of p-aminophenol, 5 g Kaiser KSA heavy-alumina and 15.1 g (0.89 mole) of ammonia with 20 ml of benzene were charged into a 300 ml stainless steel rocking autoclave. A reaction temperature of 350° C. and pressure of 1500 psig were held for one hour. Upon cooling, 0.96 g of product was recovered as described in Example IV. Gas chromatographic and mass spectral analysis of the recovered product indicated the yield of p-phenylenediamine was 46%. The balance of the product was almost entirely p-aminophenol.

p-Aminophenol conversion was 48%, lower than with the catalyst used in Example IV, indicating different alumina catalysts give different conversion rates. Selectivity was 96% but yield was lower, being 46%.

EXAMPLE VI

The procedure of Example IV was repeated with 17.3 g (1.02 moles) of ammonia with a reaction time of 4 hours. Upon cooling, 0.73 g of product was recovered. Mass spectral analysis indicated 48% yield of p-phenylenediamine at 95% conversion and 50% selectivity. Decomposition of p-aminophenol was noted.

The data indicate that after 1 hour reaction time, p-aminophenol does begin to decompose despite the presence of an inert hydrocarbon.

EXAMPLE VII

The procedure of Example IV was repeated with different reaction temperatures from approximately 250° C. to 400° C. Mole ratios of ammonia to p-aminophenol were varied from 43:1 to 100:1. The resulting data are in the following table.

TABLE I

Temperature and Concentration Effects Upon Selectivity and Yield to p-Phenylenediamine

| Run | Temp. °C. | Mole Ratio NH₃:p-AP |
|---|---|---|
| 1 | 254–263 | 100 |
| 2 | 300 | 80 |
| 3 | 353 | 92 |
| 4 | 349 | >75 |
| 5 | 354 | 91 |
| 6 | 375 | 43 |
| 7 | 370–378 | 70 |
| 8 | 375 | 98 |
| 9 | 396–401 | 95 |

| Run | Selectivity p-PDA % | Yield p-PDA % | Recovered p-AP % |
|---|---|---|---|
| 1 | 9.5 | 4 | 58 |
| 2 | 5.8 | 3 | 48 |
| 3 | 66 | 63 | 4 |
| 4 | 76 | 68 | 10 |
| 5 | 76 | 73 | 4 |
| 6 | 41 | 34 | 18 |
| 7 | 46 | 46 | 1 |
| 8 | 57 | 54 | 5 |
| 9 | 64 | 63 | 2 |

Conditions:

| | |
|---|---|
| Feed: p-Aminophenol (p-AP) | 1 g |
| Catalyst: Areo 100 gamma Alumina | 5 g |
| Hydrocarbon: Benzene | 20 ml |
| Time: | 1 Hr. |

The above data indicate that the amination of p-aminophenol (p-AP) in the presence of an inert hydrocarbon is temperature-dependent and dependent on the mole ratio of ammonia to p-aminophenol, as evidenced by the above yields and selectivities. At or below 300° C. p-phenylenediamine yield is low even with a high ammonia:p-aminophenol ratio, yield being less than 5% and selectivity less than 10%. Under conditions of the reaction as given, highest yields of p-phenylenediamine (p-PDA), approximately 60–75%, were obtained at a reaction temperature of about 350° C. and a mole ratio of ammonia to p-aminophenol of over 70:1. At 400° C. and a 95:1 mole ratio a 63% yield of p-phenylenediamine was obtained with 98% conversion and selectivity to p-phenylenediamine of 64%. The data indicate that as temperature was increased from approximately 250° C. to 400° C. and concentration of ammonia increased, conversion of p-aminophenol increased to almost 100%. Selectivity to p-phenylenediamine peaked at approximately 350° C. with an ammonia to p-aminophenol ratio of over 90:1.

EXAMPLE VIII

The procedure of Example IV was repeated using benzene, toluene, o-xylene, dodecane, dimethylformamide (DMF), methanol, acetonitrile and methylethyl ketone (MEK) in place of benzene. p-Aminophenol was used again as the reactant because it is the intermediate in preparation of p-phenylenediamine from 1,4-dihydroxybenzene. Use of other than inert materials caused side reactions, producing material that was not analyzed. Resulting data are given in Table II.

TABLE II

Effect Upon Amination of p-Aminophenol Of Inert and Reactive Compounds

| Run | Compound | Yield p-PDA % | p-PDA Selectivity % |
|---|---|---|---|
| 1 | Benzene | 68 | 76 |
| 2 | Benzene | 73 | 76 |
| 3 | Benzene | 63 | 66 |
| 4 | Toluene | 65 | 68 |
| 5 | o-Xylene | 72 | 77 |
| 6 | Dodecane | 51 | 59 |
| 7 | DMF | (DMF reacted) | |
| 8 | Methanol | (CH₃OH reacted) | |
| 9 | Acetonitrile | (CH₃CN reacted) | |
| 10 | MEK | (MEK reacted) | |

The above data indicate that only inert liquid materials boiling in the range of approximately 50°–200° C. which do not have reactive hydrogens or reactive groups are suitable.

EXAMPLE IX

Using the procedure of Example IV, four samples of p-aminophenol were run in benzene, as the inert hydrocarbon, at 350° C. for one hour with and without the presence of ammonia and with and without Areo 100 gamma alumina as catalyst. The data are presented in Table III.

TABLE III

Decomposition of p-Aminophenol in Benzene at 350° C.

| Run | Reactant | Reaction Conditions NH₃ | Catalyst | % p-AP Decomposed | % p-AP Recovered |
|---|---|---|---|---|---|
| 1 | p-AP | None | Alumina | 88 | 12 |
| 2 | p-AP | None | Alumina | 95 | 5 |
| 3 | p-AP | NH₃ | None | 32 | 68 |
| 4* | p-AP | None | None | 26 | 74 |

*Under nitrogen blanket.

The data indicate p-aminophenol severely decomposes in the presence of Areo 100 gamma alumina alone. In the presence of ammonia but without Areo 100 gamma alumina decomposition of p-aminophenol is less, 32%. In the absence of ammonia and Areo 100 gamma alumina with only inert nitrogen and benzene present, 26% of p-aminophenol decomposed.

EXAMPLE X

In the procedure of Example IV, six samples were prepared with varying ratios of p-aminophenol to alumina, Al₂O₃. All runs were performed in benzene at 350° C. in a rocking autoclave with reaction times of one hour. The resulting data are in Table IV.

TABLE IV

Effect of p-Aminophenol to Alumina Ratio

| Run | p-AP Alumina Ratio | NH₃: p-AP Ratio | Yield p-PDA % | Selectivity to p-PDA % |
|---|---|---|---|---|
| 1 | 1:5 | 97:1 | 70 | 68 |
| 2 | 1:5 | 91:1 | 73 | 76 |
| 3 | 1:5 | 92:1 | 63 | 66 |
| 4 | 1:1 | 99:1 | 70 | 72 |
| 5 | 1.0:0.2 | 107:1 | 4 | 10 |
| 6 | 1.0:0.2 | 19:1 | 2 | 3 |

The above data indicate relative concentrations of p-aminophenol and alumina catalyst affected the reaction rate and products recovered. A large amount of catalyst relative to the amount of p-aminophenol increased selectivity to p-phenylenediamine. Runs 5 and 6 indicate that high relative ratios of p-aminophenol to alumina catalyst cause product yield and selectivity to be low.

EXAMPLE XI

In the procedure of Example IV, seven samples were prepared with varying mole ratios of NH₃:p-aminophenol. All runs were performed in benzene as a solvent at 350° C. in a rocking autoclave with reaction times of one hour and a ratio of p-aminophenol to alumina of 1:5. The resulting data are in Table V.

TABLE V

Effect of NH₃:p-Aminophenol Ratio

| Run | NH₃: p-AP Mole Ratio | Yield p-PDA % |
|---|---|---|
| 1 | 20:1 | <1 |
| 2 | 27:1 | 14 |
| 3 | 45:1 | 33 |
| 4 | 75:1 | 55 |
| 5 | 99:1 | 70 |
| 6 | 91:1 | 73 |
| 7 | 92:1 | 63 |

The above data indicate that increasing the ammonia concentration relative to the concentration of the p-aminophenol increased yield to p-phenylenediamine. At an ammonia:p-aminophenol mole ratio of 20:1, p-aminophenol yield to p-phenylenediamine was less than 1%. At a ratio of about 90:1 or higher, yield increased to over 60%.

EXAMPLE XII

To a 300 ml stainless steel rocking autoclave were charged 1 g (9.2×10⁻³ moles) of p-aminophenol, 20 ml of toluene and 5 g Areo 100 gamma alumina. After the autoclave was sealed and flushed with nitrogen, followed by ammonia, 12 g (0.7 mole) of ammonia were charged into the autoclave. The autoclave was then heated to 350° C. for one hour during which time an internal pressure of 1200 psig was generated. After one hour at 350° C. the autoclave was allowed to cool for several hours, the excess pressure vented and the contents removed. The catalyst was recovered by filtration and washed with benzene and methanol to remove any organic material. The solvent was removed by distillation leaving 0.88 g of solid product. Silylation gas chromatographic and mass spectral analysis of the product indicated that 74% of the 0.88 g of recovered solid was p-phenylenediamine.

The above results indicated that toluene is a suitable inert hydrocarbon.

EXAMPLE XIII

The following Examples XIII and XIV illustrate the results obtained if no inert hydrocarbon is employed.

To a 300 ml stainless steel rocking autoclave 1 g (9.2×10⁻³ moles) p-aminophenol and 5 g Areo 100 gamma alumina were charged. No inert hydrocarbon was employed. After the autoclave was sealed and flushed with nitrogen, followed by ammonia, 18.4 g (1.08 moles) ammonia were charged into the autoclave. The autoclave was then heated to 350° C. for one hour after which it was cooled, the excess ammonia vented and the contents removed. The product in low purity was recovered from the mixture by repeated washing with methanol. The solvent was removed and the product analyzed by silylation gas chromatography.

The overall yield of p-phenylenediamine was 33.9% at 86% p-aminophenol conversion based on the original 1 g sample. Approximately 52% of the p-aminophenol starting material was converted to undesirable by-products. Approximately 14% of the p-aminophenol starting material was unreacted. Selectivity of about 39% to p-phenylenediamine and recovery of product were much less than in examples wherein inert hydrocarbons were used.

In addition to the yield of 33.9% of p-phenylenediamine based on weight of starting material, at least 8 (in number) by-products of an unidentified nature were present in the dark tar-like product. Only 70% of the product was eluted from the gas chromatograph column indicating side reactions giving higher molecular weight products had occurred.

EXAMPLE XIV

One gram ($9.2 \times 10^{-3}$ moles) 1,4-dihydroxybenzene, 5 g Areo 100 gamma alumina and excess ammonia were charged into a 300 ml stainless steel autoclave. No inert hydrocarbon was employed. A reaction temperature of 350° C. was held for one hour. Upon cooling, 0.88 g of product was recovered as described in Example XIII. Silylation gas chromatograhic analysis indicated an approximate 0.8% yield of p-phenylenediamine and an approximate 11% yield of p-aminophenol at 90.3% 1,4-hydroxybenzene conversion. Approximately 78% of the starting material of 1,4-dihydroxybenzene was converted to undesirable by-products. At least 18 (in number) by-products were present according to the analysis. Approximately 9.7% of the 1,4-dihydroxybenzene starting material was unreacted.

The above results in Examples XIII and XIV show the resulting uneconomic and poor yields obtained when 1,4-dihydroxybenzene is aminated according to the procedures taught in U.S. Pat. No. 3,860,650 and Japanese Pat. Nos. 74-14737 and 74-13738.

What is claimed is:

1. A process for the amination of a hydroxy aromatic selected from the group consisting essentially of 1,4-dihydroxybenzene and p-aminophenol which comprises reacting said hydroxy aromatic with an aminating agent in the presence of an inert liquid hydrocarbon with a boiling point in the range of from about 25° C. to 400° C., and an alumina catalyst selected from the group consisting of alpha alumina, gamma alumina and eta alumina catalysts at a temperature within the range of from about 300° C. to 450° C., a pressure from atmospheric to about 3000 psig wherein the concentration of said catalyst is within the range of from about 1:1 to about 1:10, weight of hydroxy aromatic to weight of catalyst and the mole ratio of aminating agent as ammonia to reactant is at least 20:1, aminating agent to reactant.

2. The process of claim 1 wherein said aminating agent is selected from the group consisting of ammonia, ammonium chloride, ammonium bromide, ammonium iodide, ammonium hydroxide, ammonium nitrate, ammonium carbonate, methylamine, dimethylamine, ethylamine and diethylamine.

3. The process of claim 2 wherein said aminating agent is ammonia.

4. The process of claim 1 wherein the mole ratio of aminating agent as ammonia to reactant is within the range of about 70:1 to about 150:1, aminating agent to reactant.

5. The process of claim 1 wherein said inert hydrocarbon is selected from the group consisting of benzene, toluene, xylene, cyclohexane, hexane, heptane, octane, nonane and decane.

6. The process of claim 1 wherein the said catalyst is selected from the group consisting of alpha alumina catalysts, gamma alumina catalysts, eta alumina catalysts and silica-alumina catalysts.

7. The process of claim 1 wherein the concentration of said catalyst is within the range of from about 1:1 to about 1:5, weight of hydroxy aromatic to weight of catalyst.

8. The process of claim 1 wherein temperature is within the range of from about 325° C. to about 400° C.

* * * * *